United States Patent [19]

Chiyomaru et al.

[11] 4,105,693
[45] Aug. 8, 1978

[54] PROCESS FOR PRODUCING 2-ALKYLBENZANILIDE

[75] Inventors: Isao Chiyomaru, Shimizu; Seigo Kawada, Fujieda; Kiyoshi Takita, Shimizu, all of Japan

[73] Assignee: Kumiai Chemical Industry Co., Ltd., Tokyo, Japan

[21] Appl. No.: 679,370

[22] Filed: Apr. 22, 1976

Related U.S. Application Data

[60] Continuation-in-part of Ser. No. 605,050, Aug. 15, 1975, Pat. No. 3,985,804, which is a division of Ser. No. 489,412, Jul. 11, 1974, Pat. No. 3,937,840.

[30] Foreign Application Priority Data

Aug. 18, 1973 [JP] Japan .................................. 48-92702

[51] Int. Cl.$^2$ ............................................ C07C 103/78
[52] U.S. Cl. .................................. 260/558 P; 424/324
[58] Field of Search ..................................... 260/558 P

[56] References Cited

U.S. PATENT DOCUMENTS

| | | | |
|---|---|---|---|
| 3,462,486 | 8/1969 | De Feo | 260/558 P X |
| 3,937,840 | 2/1976 | Chiyomaru et al. | 424/324 |

FOREIGN PATENT DOCUMENTS 1,217,868  12/1970  United Kingdom.

*Primary Examiner*—Winston A. Douglas
*Assistant Examiner*—Thomas A. Waltz
*Attorney, Agent, or Firm*—Oblon, Fisher, Spivak, McClelland & Maier

[57] ABSTRACT

2-Alkylbenzanilide is produced by reacting an alkyl 2-alkylbenzoate having the formula

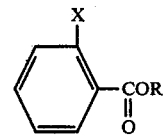

wherein X represents a lower alkyl group and R represents a lower alkyl group with an aniline having the formula

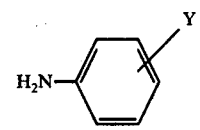

wherein Y represents hydrogen atom, an alkoxy, alkenyloxy, alkynyloxy, benzyloxy or halobenzyloxy group in the presence of an alcoholate in a solvent which is hardly azeotropically distilled with the by-product of alcohol.

20 Claims, No Drawings

PROCESS FOR PRODUCING 2-ALKYLBENZANILIDE

CROSS REFERENCE TO RELATED APPLICATIONS

This application is a continuation-in-part of application Ser. No. 605,050, filed Aug. 15, 1975, now U.S. Pat. No. 3,985,804, which is a divisional of Ser. No. 489,412, filed July 17, 1974, now U.S. Pat. No. 3,937,840.

BACKGROUND OF THE INVENTION

The present invention relates to a process for producing 2-alkylbenzanilide which is useful as agricultural germicide.

More particularly, it relates to an improved industrial process for producing 2-alkylbenzanilide having high purity by reacting an alkyl 2-alkylbenzoate with aniline or an aniline derivative.

The 2-alkylbenzanilides have high-germicidal effect and broad antimicrobial spectrum and are effective in preventing diseases, such as rice sheath blight, bacterial leaf blight, tomato late blight, cucumber anthracnose, haricot stem rot, alternaria leaf spot, powdery apple mildew, orange phoma rot, wheat bund, rusting of wheat, barley, turf, coffee, ornamental plants, vegetables, cereals and grasses, smut and Rhizoctonia and Fusarium soil diseases; and are also effective as disinfectants for seeds. It has been known to produce benzanilides having no substituent on benzene nucleus of benzoyl group by reacting an alkyl benzoate having no substituent on benzene nucleus with an aniline in the presence of an alcoholate e.g. sodium methylate in an organic solvent of a by-product of alcohol in an azeotropic condition.

For example, in Richard J. De Foo et al., Journal of Organic Chemistry Vol. 28, P 2915 (1963) and U.S. Pat. No. 3,462,486, benzanilides are produced by reacting ethyl benzoate with an aniline in benzene and a by-product of ethyl alcohol in an azeotropic condition in the presence of solid sodium methylate as shown in the following equation.

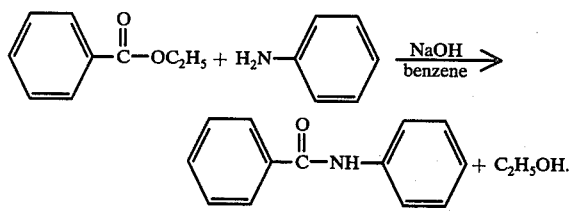

In order to smoothly proceed a condensation reaction of an alkyl carboxylate with an aniline, it is necessary to easily remove a by-product of alcohol out of a reaction system. Accordingly, it has been considered that the optimum condition is to use an organic solvent which is azeotropically distilled with the by-product of alcohol. Benzene has been used as the organic solvent.

However, it has been hard to produce 2-alkyl benzanilides having high germicidal effect and broad antimicrobial spectrum in high yield by the conventional processes. That is, it has been hard to produce 2-alkylbenzanilide in high yield by reacting alkyl 2-alkyl benzoates which have a substituent at orth position to alkoxy carbonyl group with an aniline. In said processes, N-alkyl benzanilides have been easily produced as by-product, and it has been hard to completely inhibit the formation of the by-product.

When 2-alkylbenzanilide is contained with the by-product, the germicidal effect of 2-alkylbenzanilide may be adversely affected.

The inventors have studied to improve the conventional processes to inhibit the formation of the by-product of N-alkylbenzanilide so as to produce 2-alkylbenzanilides which have high germicidal effect and broad antimicrobial spectrum in high yield.

As the results, the inventors have found that the optimum condition is to react an alkyl 2-alkylbenzoate with an aniline in an organic solvent which is hardly azeotropically distilled with the by-product of alcohol.

The inventors have also found that the reactivity is different depending upon carbon atoms of the alkyl group of alkoxy carbonyl group of the alkyl 2-alkylbenzoate.

As the result of further studies, the inventors have found that 2-alkylbenzanilides can be produced in high yield without the formation of the by-product of N-alkylbenzanilide by reacting an alkyl 2-alkylbenzoate having the alkoxy carbonyl group having specific carbon atoms with an aniline in the presence of specific alcoholate in an organic solvent which is hardly azeotropically distilled with the by-product of alcohol.

SUMMARY OF THE INVENTION

It is an object of the present invention to provide a process for producing 2-alkylbenzanilide in high yield without formation of a by-product of N-alkylbenzanilide.

The object of the invention has been attained by producing 2-alkylbenzanilide having the formula

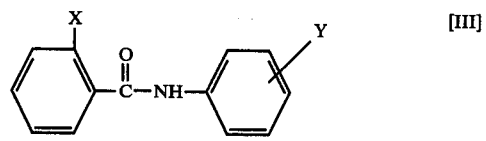

wherein X represents a lower alkyl group and Y represents hydrogen atom, an alkoxy, alkenyloxy, alkinyloxy, benzyloxy, or halobenzyloxy group, by reacting an alkyl 2-alkylbenzoate having the formula

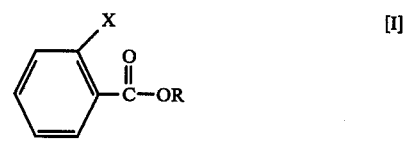

wherein R represents a $C_{1-4}$ alkyl group with an aniline having the formula

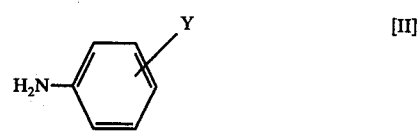

in the presence of an alcoholate in an organic solvent which is hardly azeotropically distilled with the by-product of alcohol.

DETAILED DESCRIPTION OF THE EMBODIMENTS

The alkyl 2-alkylbenzoates can be the compound having the formula [I] wherein X is a lower alkyl group such as methyl, ethyl, propyl, iso-propyl, n-butyl, sec-butyl, iso-butyl or tert-butyl group; and R is a $C_{1-4}$ alkyl group such as methyl, ethyl, n-propyl, iso-propyl, n-butyl, sec-butyl, iso-butyl or tert-butyl, and preferably a $C_{2-4}$ alkyl group.

When R is methyl group, N-methylbenzanilide is formed as the by-product. When R is an alkyl group having more than 5 carbon atoms or a phenyl group, the yield of 2-alkylbenzanilide is relatively low.

The anilines can be the compound having the formula [II] wherein Y is hydrogen atom, an alkoxy group such as methoxy, ethoxy, n-propoxy, iso-propoxy, n-butoxy, sec-butoxy, iso-butoxy, tert-butoxy, pentyloxy, iso-pentyloxy, hexyloxy, octyloxy, or dodecyloxy group; and an alkenyloxy group such as vinyloxy, allyloxy or 1-methylallyloxy group and an alkynyloxy group such as acetyleneoxy, propargyloxy, 1-propylpropargyloxy group and benzyloxy group or halobenzyloxy group such as chlorobenzyloxy group.

The alcoholates used in the process of the invention are alkali metal alcoholates and alkaline earth metal alcoholates such as potassium methylate, sodium ethylate, sodium n-propylate, sodium-iso-propylate, potassium ethylate, potassium n-propylate, potassium-iso-propylate and the like.

When methylate is used, N-methylbenzanilides are produced as the by-product.

When methylate is used in the case of the compound having the formula [I] wherein R is methyl group, a large amount of N-methylbenzanilide is produced.

The solvent which is quite important in the invention is preferably a compound having the formula

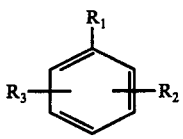

[IV]

wherein $R_1$ represents a lower alkyl group or chlorine atom; $R_2$ represents hydrogen atom, a lower alkyl group or chlorine atom, and $R_3$ represents hydrogen atom, a lower alkyl group or chlorine atom, or a compound having the formula

$R_4 - O - R_5$  [V]

wherein $R_4$ and $R_5$ respectively represent alkyl groups having more than 5 carbon atoms. Suitable solvents include the compounds having the formula [IV] wherein (1) $R_1$ is methyl, $R_2$ is a $C_{1-4}$ alkyl group or Cl and $R_3$ is H or Cl or (2) $R_1$ is Cl, $R_2$ is H or Cl and $R_3$ is H or (3) $R_1$ is a $C_{2-5}$ alkyl group and $R_2$ and $R_3$ are H, and the compounds having the formula [V] wherein $R_4$ and $R_5$ are $C_{5-6}$ alkyl groups.

The typical solvents include o-, m- and p-xylene, o-, m- and p-ethyltoluene; o-, m- and p-propyltoluene; o-, m- and p-cymene; o-, m- and p-chlorotoluene; 2,4-, 2,5- and 2,6-dichlorotoluene; 3,4-dichlorotoluene, chlorobenzene, o-dichlorobenzene, m-dichlorobenzene, ethylbenzene, n-propylbenzene, cumene, n-butylbenzene, iso-butylbenzene, sec-butylbenzene, tert-butylbenzene, n-amylbenzene, iso-amylbenzene, tert-amylbenzene, mesitylene, diethylbenzene, n- or iso-dibutyl ether, n-amyl ether, iso-amyl ether, and like.

When the solvent of o-, m-, or p-xylene, or chlorobenzene is used in the case that R in the compound [I] is n-propyl group; or the solvent of o-, m-, or p-xylene, ethylbenzene or chlorobenzene is used in the case that R of the compound [I] is n-butyl group or the solvent of o-xylene, ethylbenzene or chlorobenzene is used in the case that R of the compound [I] is iso-butyl group, an azeotropic distillation is caused with the by-product of the alcohol formed by the reaction in some degree.

The other solvents cause disadvantage as follows.

When benzene or toluene is used, an azeotropic distillation is caused with the by-product of the alcohol formed in the reaction, whereby it is hard to produce 2-alkylbenzanilide in high yield.

When dimethylformamide is used, it reacts with the anilines to produce the by-products of formamidines.

When alcohols and lower alkyl ethers are used, the reaction is not smoothly proceeded or yield of the product is not satisfactorily high.

When chlorohydrocarbon such as chloroform is used, the side reaction is caused.

The reaction of the invention is usually carried out by reacting the alkyl 2-alkylbenzoate [I] with the aniline-[II] under atmospheric pressure in the presence of the specific alcoholate in the specific solvent with stirring under heating.

For example, the alkyl o-alkylbenzoate [I] is added to a mixture of the specific alcoholate and the aniline [II] in the specific solvent with stirring under heating or the specific alcoholate is added to a mixture of the alkyl 2-alkylbenzoate [I] and the aniline [II] in the specific solvent. It is not preferable to admix the alkyl 2-alkylbenzoate with the specific alcoholate at first.

The amount of the alkyl 2-alkylbenzoate [I] is usually in a range of 0.9 to 1.5 mole preferably 1 to 1.3 mole per 1 mole of the aniline [II]. The amount of the specific alcoholate is usually in a range of 0.9 to 2.0 mole preferably 1 to 1.5 mole per 1 mole of the aniline [II]. The reaction temperature is in a range of 100° to 200° C preferably 120° to 150° C.

The reaction time is in a range of 1 to 20 hours preferably 2 to 6 hours.

After the reaction, the object product of 2-alkylbenzanilides are produced in the form of alkali metal or alkaline earth metal salts. It is usual to add a mineral acid for hydrolysis of metal salts of benzanilides.

However, in accordance with the process of the invention, it is possible to hydrolyze the metal salts of 2-alkylbenzanilides by adding water to the reaction mixture, whereby 2-alkylbenzanilides [III] can be separated in high yield.

The followings are the characteristics and advantages of the invention.

Firstly, 2-alkylbenzanilides which are useful as germicides and had been hard to be produced in high yield can be produced in high yield.

Secondly, 2-alkylbenzanilides can be produced in high yield while inhibiting the formation of by-product of N-alkylbenzanilides.

As N-alkylbenzanilide is not included in the product, the product of 2-alkylbenzanilide can be used as germicide with stable and high germicidal effect.

The invention will be further illustrated by certain examples and comparative references in detail.

EXAMPLE 1

Preparation of 3'-iso-propoxy-2-methylbenzanilide

In a 200 ml four necked flask equipped with a stirrer, a thermometer, a condenser and a dropping funnel, 50 ml of p-xylene, 15.1 g (0.1 mol) of m-iso-propoxyaniline and 37.4 g of 20% ethyl alcohol solution of sodium ethyl alcoholate (0.11 mol as $NaOC_2H_5$) were charged. The mixture was heated at 80° to 90° C to distill ethyl alcohol.

The mixture was heated to 130° C and 19.6 g (0.11 mol) of isopropyl 2-methylbenzoate was added dropwise to the mixture at 130° C during 30 minutes with stirring and the reaction was further continued for 5 hours. The by-product of isopropyl alcohol formed by the addition of isopropyl 2-methylbenzoate was distilled off in the reaction.

After the reaction, the reaction mixture was cooled and 50 ml of water was added to the reaction mixture and 50 ml of n-hexane was added and the precipitated crystals were filtered to obtain 25.6 g (yield 95.2%) of white crystals of 3'-isopropoxy-2-methylbenzanilide (m.p. 91° to 92° C). According to gas chromatography analysis, it was confirmed that a by-product of N-alkyl-3-isopropoxy-2-methylbenzanilide was not formed. The purity of the product was 99.8%.

EXAMPLE 2

In accordance with the process of Example 1, the reactions of various alkyl 2-methylbenzoates with m-isopropoxyaniline were carried out in various solvents of p-xylene, ethylbenzene and chlorobenzene. As the results, when methyl 2-methylbenzoate was used, N-methyl-3'-isopropoxy-2-methylbenzanilide was produced as by-product in all solvents. The yields of 3'-isopropoxy-2-methylbenzanilides in the reactions are as follows.

Table 1

| Experiment No. | R | Organic solvent (yield %) | | |
|---|---|---|---|---|
| | | p-xylene | ethyl benzene | chlorobenzene |
| 1 | $-CH_3$ | 73.6 | 72.3 | 74.9 |
| 2 | $-CH_2CH_3$ | 93.1 | 92.1 | 91.2 |
| 3 | $-CH_2CH_2CH_3$ | 80.1 | 93.7 | 79.9 |
| 4 | $-CH(CH_3)_2$ | 95.2 | 94.0 | 94.6 |
| 5 | $-(CH_2)_3CH_3$ | 79.1 | 78.3 | 72.7 |
| 6 | $-CHCH_2CH_3$<br>$\|$<br>$CH_3$ | 93.5 | 92.7 | 93.3 |
| 7 | $-CH_2CH(CH_3)_2$ | 93.8 | 78.6 | 74.4 |
| 8 | $-C(CH_3)_3$ | 97.3 | 95.9 | 96.7 |
| 9 | $-(CH_2)_4CH_3$ | 64.1 | 65.1 | 66.4 |
| 10 | $-(CH_2)_2CH(CH_3)_2$ | 66.5 | 67.3 | 67.0 |
| 11 | phenyl | 65.9 | 66.3 | 63.1 |

As shown in Example 2, when p-xylene was used as the solvent in the case that R is n-propyl or n-butyl group, the yield was low. When ethylbenzene was used as the solvent in the case that R is n-propyl or n-butyl group, the yield was low.

When chlorobenzene was used in the case that R is n-propyl, n-butyl or iso-butyl group, the yield was low.

Thus, in accordance with the process of Example 2, the reactions were carried out by using p-cymene, cumene or mesitylene.

As the results, the yields were not decreased, and 3'-isopropoxy-2-methylbenzanilide could be obtained in high yield of more than 90% except the cases that R is methyl, n-amyl or isoamyl group.

EXAMPLE 3

Preparation of 4'-methoxy-2-methylbenzanilide

In the flask of Example 1, 50 ml of cumene, 13.7 g (0.1 mol) of p-ethoxyaniline and 37.4 g of 20% of ethyl alcohol solution of sodium ethylate (0.11 mol as $NaOC_2H_5$) were charged. The mixture was heated at 80° to 90° C to distill off ethyl alcohol and 18.1 g (0.11 mol) of ethyl 2-methylbenzoate was added dropwise to the mixture at 130° C during 30 minutes with stirring, and the reaction was further continued for 5 hours. The by-product of ethyl alcohol formed by the addition of ethyl 2-methylbenzoate was distilled off in the reaction.

After the reaction, the reaction mixture was treated in accordance with the process of Example 1 to obtain 25.0 g (yield 92.9%) of white needles of 4-methoxy-2-methylbenzanilide (m.p. 149° to 149.5° C).

EXAMPLE 4

In accordance with the process of Example 3, the reactions of various alkyl 2-methylbenzoates with p-ethoxyaniline were carried out in the presence of various alcoholates in various solvents to produce the corresponding 2-alkylbenzanilides.

The results are shown in Table 2.

Table 2

| Experiment No. | R | Alcoholate | Organic solvent | Yield (%) |
|---|---|---|---|---|
| 1 | $-C_2H_5$ | $NaOC_3H_7$-n | n-propyl benzene | 91.9 |
| 2 | $-CH_2CH_2CH_3$ | $NaOC_2H_5$ | p-cymene | 93.2 |
| 3 | $-CH(CH_3)_2$ | $NaOC_2H_5$ | ethyl toluene | 92.9 |
| 4 | $-(CH_2)_3CH_3$ | $NaOC_2H_5$ | mesitylene | 93.7 |
| 5 | $-CHCH_2CH_3$<br>$\|$<br>$CH_3$ | $NaOC_2H_5$ | di-n-butyl ether | 91.6 |
| 6 | $-CH_2CH(CH_3)_2$ | $NaOC_2H_5$ | p-cymene | 93.8 |
| 7 | $-C(CH_3)_3$ | $NaOC_2H_5$ | d-n-amyl ether | 92.2 |
| 8 | $-C(CH_3)_3$ | $NaOC_2H_5$ | 2,3-di-chloro toluene | 93.5 |
| Ref. 1 | $-CH_3$ | $NaOCH_3$ | benzene | 31.8 |
| Ref. 2 | $-C_2H_5$ | $NaOC_2H_5$ | benzene | 39.9 |
| Ref. 3 | $-C_2H_5$ | $NaOC_2H_5$ | toluene | 48.0 |
| Ref. 4 | $-C_2H_5$ | $NaOC_2H_5$ | DMF | 8.2 |
| Ref. 5 | $-C_2H_5$ | $NaOC_2H_5$ | DMSO | 42.9 |

Table 2-continued

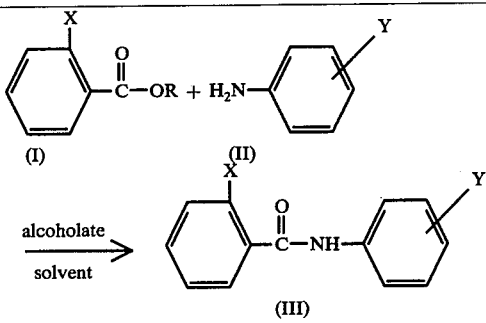

| Experiment No. | R | Alcoholate | Organic solvent | Yield (%) |
|---|---|---|---|---|
| Ref. 6 | —$C_2H_5$ | $NaOC_2H_5$ | — | 65.8 |

Note:
[1] In References 1 and 2, the reaction was carried out by azeotropically distilling off the by-product of alcohol and benzene under refluxing. In Reference 1, N-methyl-4'-ethoxy-2-methylbenzanilide was produced as by-product.
[2] In Reference 3, the reaction was carried out by azeotropically distilling off the by-product of ethyl alcohol and toluene under refluxing.
[3] In References 4 and 5, the reaction was carried out at 130° C. The by-product was produced.
[4] In Reference 6, the reaction was carried out at 170° C without a solvent. The by-product was produced.

EXAMPLE 5

In accordance with the process of Example 1, the reactions of various alkyl 2-alkylbenzoate with various anilines were carried out in the presence of various alcoholates in various solvents to produce the corresponding 2-alkylbenzanilides.

The results are shown in Table 3.

Table 3

$$\underset{(I)}{\overset{X}{\text{benzoate}}}-C(=O)-OR + H_2N-\underset{(II)}{\overset{Y}{\text{aniline}}} \xrightarrow[\text{solvent}]{\text{alcoholate}} \underset{(III)}{\overset{X}{\text{product}}}-C(=O)-NH-\text{aniline}-Y$$

Conditions of Reactions:

| Experiment No. | Benzoate (I) | Aniline (II) | Alcoholate (amount) | Solvent | Reaction temp. (° C) |
|---|---|---|---|---|---|
| 1 | X = $CH_3$<br>R = $C_2H_5$<br>18.1 g<br>(0.11 mol) | Y = H<br><br>9.3 g<br>(0.1 mol) | $NaOC_2H_5$<br>(20%)<br>37.4 g<br>(0.11 mol) | p-xylene | 130 |
| 2 | X = $C_2H_5$<br>R = iso-$C_4H_9$<br>22.7 g<br>(0.11 mol) | Y = H<br><br>9.3 g<br>(0.1 mol) | $NaOC_2H_5$<br>(20%)<br>37.4 g<br>(0.11 mol) | p-cymene | 150 |
| 3 | X = i-$C_3H_7$<br>R = t-$C_4H_9$<br>24.2 g<br>(0.11 mol) | Y = H<br><br>9.3 g<br>(0.1 mol) | $NaOC_2H_5$<br>(20%)<br>37.4 g<br>(0.11 mol) | p-xylene | 130 |
| 4 | X = $CH_3$<br>R = n-$C_3H_7$<br>19.6 g<br>(0.11 mol) | Y = $OCH_3$<br>at meta<br>12.3 g<br>(0.1 mol) | $NaOC_3H_7$<br>(20%)<br>45.1 g<br>(0.11 mol) | o-cymene | 150 |
| 5 | X = $CH_3$<br>R = s-$C_4H_9$<br>21.1 g<br>(0.11 mol) | Y = $OC_3H_7$<br>at para<br>15.1 g<br>(0.1 mol) | $NaOC_2H_5$<br>(20%)<br>37.4 g<br>(0.11 mol) | p-xylene | 130 |
| 6 | X = $CH_3$<br>R = i$C_3H_7$<br>22.7 g<br>(0.11 mol) | Y = s-$OC_4H_9$<br>at meta<br>16.5 g<br>(0.1 mol) | NaOi-$C_3H_7$<br>(10%)<br>90.3 g<br>(0.11 mol) | p-cymene | 150 |
| 7 | X = $CH_3$<br>R = $C_2H_5$<br>18.1 g<br>(0.11 mol) | Y = n.$OC_4H_9$<br>at meta<br>16.5 g<br>(0.1 mol) | $NaOC_2H_5$<br>(20%)<br>37.4 g<br>(0.11 mol) | chlorobenzene | 125 |
| 8 | X = $CH_3$<br>R = $C_2H_5$<br>18.1 g<br>(0.11 mol) | Y = s-$OC_5H_{11}$<br>at meta<br>17.9 g<br>(0.1 mol) | $NaOC_2H_5$<br>(20%)<br>37.4 g<br>(0.11 mol) | ethyl benzene | 130 |
| 9 | X = $CH_3$<br>R = $C_2H_5$<br>18.1 g<br>(0.11 mol) | Y = $OCH_2$.Ph<br>at meta<br>19.9 g<br>(0.1 mol) | $NaOC_2H_5$<br>(20%)<br>37.4 g<br>(0.11 mol) | mesitylene | 150 |
| 10 | X = $CH_3$<br>R = $C_2H_5$<br>18.1 g<br>(0.11 mol) | Y = $OCH_2PhCl$<br>at meta<br>23.3 g<br>(0.1 mol) | $NaOC_2H_5$<br>(20%)<br>37.4 g<br>(0.11 mol) | chlorobenzene | 125 |

Products (III)

| Experiment No. | Product | Amount (g) | Yield (%) | Melting point (° C) | Crystals |
|---|---|---|---|---|---|
| 1 | X = $CH_3$<br>Y = H | 19.5 | 92.4 | 125–126 | white powder |
| 2 | X = $C_2H_5$ | 20.4 | 90.7 | 141–142 | " |

Table 3-continued

| | | | | | |
|---|---|---|---|---|---|
| 3 | Y = H<br>X = iso-C$_3$H$_7$ | 20.3 | 84.9 | 135-136 | " |
| 4 | Y = H<br>X = CH$_3$<br>Y = OCH$_3$<br>at meta | 22.3 | 92.1 | 74-75 | white prism |
| 5 | X = CH$_3$<br>Y = OC$_3$H$_7$<br>at para | 25.7 | 95.5 | 151-152 | white powder |
| 6 | X = CH$_3$<br>Y = sec-C$_4$H$_9$<br>at meta | 26.3 | 92.9 | 75-77 | white needle |
| 7 | X = CH$_3$<br>Y = nOC$_4$H$_9$<br>at meta | 27.4 | 96.8 | 87 | gray needle |
| 8 | X = CH$_3$<br>Y = secOC$_5$H$_{11}$<br>at meta | 27.7 | 93.3 | 70-73 | pale brown |
| 9 | X = CH$_3$<br>Y > OCH$_2$—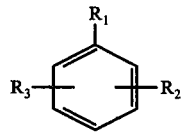<br>at meta | 28.3 | 89.3 | 114-115 | white needle |
| 10 | X = CH$_3$<br>Y = OCH$_2$—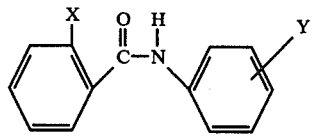<br>at meta | 31.0 | 88.1 | 115-116 | " |

We claim:

1. In a process for producing 2-alkylbenzanilide having the formula:

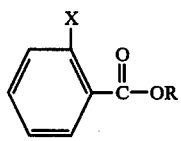

wherein X represents a C$_{1-4}$ alkyl group and Y represents hydrogen, alkoxy, alkenyloxy, alkinyloxy, benzyloxy or halobenzyloxy, with the liberation of alcohol and N-alkylbenzanilide by-products, by reacting an alkyl 2-alkylbenzoate of the formula:

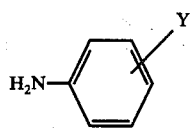

wherein R is a C$_2$-C$_4$ alkyl group and X is as defined above with an aniline compound of the formula:

wherein Y is as defined above, the improvement comprising: reacting said benzoate with said aniline compound in an organic solvent of the formula:

or R$_4$—O—R$_5$, wherein R$_1$ is lower alkyl or halogen; R$_2$ and R$_3$ are hydrogen, halogen or lower alkyl and R$_4$ and R$_5$ represent alkyl of more than 5 carbon atoms, in the presence of an alkali metal or alkaline earth metal alcoholate excluding methylate as an alcoholate, with the proviso that toluene is excluded from said organic solvent and with the proviso that when R is n-propyl, said solvent excludes o-, m-, and p-xylene and chlorobenzene; when R is n-butyl, said solvent excludes o-, m-, and p-xylene, ethylbenzene and chlorobenzene and when R is iso-butyl, said solvent excludes o-xylene, ethylbenzene and chlorobenzene, such that said reaction occurs without azeotropic separation of said solvent and the alcohol by-product released in said reaction and with the inhibition of the formation of said N-alkylbenzanilide.

2. The process according to claim 1, wherein said alcoholate is an alkali metal or alkaline earth metal alcoholate of 2 to 4 carbon atoms.

3. The process according to claim 1, wherein the alcoholate is sodium or potassium ethylate, sodium or potassium n- or iso-propylate, or sodium or potassium n-, iso, sec, or tert-butylate and the solvent is o-, m-, or p-xylene, ethylbenzene, propylbenzene, isopropylbenzene, o-, m-, or p-cymene, trimethylbenzene, n- or isobutylbenzene, amylbenzene, o-, m-, or p-chlorotoluene, 2,4-, 2,5-, 2,6- or 3,4-dichlorotoluene, chlorobenzene, o-, m-, or p-dichlorobenzene, n- or iso-dibutyl ether or n- or iso-amyl ether.

4. The process according to claim 1, wherein the reaction is carried out at 100° to 200° C.

5. The process according to claim 4, wherein the reaction is carried out at 120° to 150° C.

6. The process according to claim 1, wherein the molar ratio of the alkyl 2-alkylbenzoate [I] to the aniline [II] is in a range of 0.9 to 1.5.

7. The process according to claim 1, wherein the molar ratio of the alcoholate to the aniline [II] is in a range of 0.9 to 2.0.

8. The process according to claim 1, wherein 2-methylbenzanilide having the formula

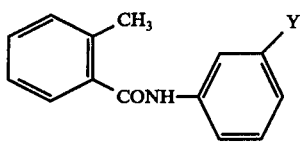

wherein Y represents an alkoxy group is produced.

9. The process according to claim 8, wherein Y represents a branched alkoxy group.

10. The process according to claim 9, wherein Y represents iso-propoxy, iso-butoxy, sec-butoxy, tert-butoxy, iso-pentyloxy or sec-pentyloxy group.

11. In a process for producing 2-alkylbenzanilide having the formula:

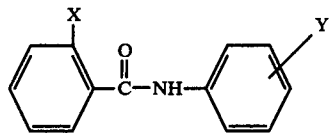

wherein X represents a $C_{1-4}$ alkyl group and Y represents hydrogen, alkoxy, alkenyloxy, alkinyloxy, benzyloxy or halobenzyloxy, with the liberation of alcohol and N-alkylbenzanilide by-products, by reacting an alkyl 2-alkylbenzoate of the formula:

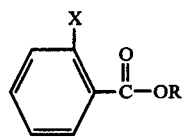

wherein R is a $C_2$-$C_4$ alkyl group and X is as defined above with an aniline compound of the formula:

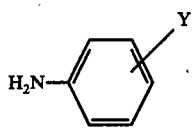

wherein Y is as defined above, the improvement comprising:

(a) reacting said aniline compound in an organic solvent of the formula:

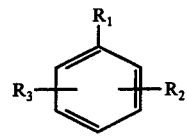

or $R_4$—O—$R_5$, wherein $R_1$ is lower alkyl or halogen; $R_2$ and $R_3$ are hydrogen, halogen or lower alkyl and $R_4$ and $R_5$ represent alkyl of more than 5 carbon atoms with an alkali metal or alkaline earth metal alcoholate excluding methylate as an alcoholate, with the proviso that toluene is excluded from the organic solvent and with the proviso that when R is n-propyl, said solvent excludes o-, m-, and p-xylene and chlorobenzene; when R is n-butyl, said solvent excludes o-, m-, and p-xylene, ethylbenzene and chlorobenzene and when R is iso-butyl, said solvent excludes o-xylene, ethylbenzene and chlorobenzene; and (b) preparing said 2-alkylbenzanilide product by reacting said alkyl 2-alkylbenzoate with the reaction product of step (a) such that said reaction occurs without azeotropic separation of said solvent and the alcohol by-product released in said reaction and with the inhibition of the formation of said N-alkylbenzanilide.

12. The process according to claim 11, wherein the alcoholate is sodium or potassium ethylate, sodium or potassium n- or iso-propylate, or sodium or potassium n-, iso, sec, or tert-butylate and the solvent is o-, m-, or p-xylene, ethylbenzene, propylbenzene, isopropylbenzene, o-, m-, or p-cymene, trimethylbenzene, n- or iso-butylbenzene, amylbenzene, o-, m-, or p-chlorotoluene, 2,4-, 2,5-, 2,6-, or 3,4-dichlorotoluene, chlorobenzene, o-, m-, or p-dichlorobenzene, n- or iso-dibutyl ether or n- or iso-amyl ether.

13. The process according to claim 11, wherein the reaction is carried out at 100° to 200° C.

14. The process according to claim 13, wherein the reaction is carried out at 120° to 150° C.

15. The process according to claim 11, wherein a molar ratio of the alkyl 2-alkylbenzoate (I) to the aniline (II) is in a range of 0.9 to 1.5.

16. The process according to claim 11, wherein a molar ratio of the alcoholate to the aniline (II) is in a range of 0.9 to 2.0.

17. The process according to claim 11, wherein 2-methylbenzanilide having the formula

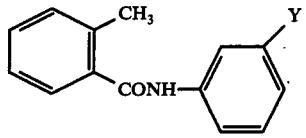

wherein Y represents an alkoxy group is produced.

18. The process according to claim 17, wherein Y represents a branched alkoxy group.

19. The process according to claim 18, wherein Y represents iso-propoxy, iso-butoxy, sec-butoxy, tert-butoxy, iso-pentyloxy or sec-pentyloxy group.

20. The method of claim 11, wherein the alkyl radical of said alcoholate is the same as the alkyl group R of said alkyl 2-alkylbenzoate.

* * * * *